tice: Subject to any disclaimer, the term of this patent is extended or adjusted under 35 U.S.C. 154(b) by 0 days.

(12) United States Patent
Awad et al.

(10) Patent No.: US 10,052,302 B2
(45) Date of Patent: *Aug. 21, 2018

(54) **GREEN SYNTHESIS OF REDUCED GRAPHENE OXIDE SILICA NANOCOMPOSITE USING *NIGELLA SATIVA* SEEDS EXTRACT**

(71) Applicant: KING SAUD UNIVERSITY, Riyadh (SA)

(72) Inventors: Manal Ahmed Gasmelseed Awad, Riyadh (SA); Awatif Ahmed Hendi, Riyadh (SA); Khalid Mustafa Osman Ortashi, Riyadh (SA); Amel Laref, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

This patent is subject to a terminal disclaimer.

(21) Appl. No.: 15/151,459

(22) Filed: May 10, 2016

(65) Prior Publication Data

US 2017/0326097 A1  Nov. 16, 2017

(51) Int. Cl.
*A61K 31/336* (2006.01)
*A61K 9/16* (2006.01)
*A61K 33/00* (2006.01)

(52) U.S. Cl.
CPC ............ *A61K 31/336* (2013.01); *A61K 9/16* (2013.01); *A61K 33/00* (2013.01)

(58) Field of Classification Search
None
See application file for complete search history.

(56) References Cited

U.S. PATENT DOCUMENTS

2012/0295027 A1  11/2012  Liu et al.
2013/0240439 A1  9/2013  Pradeep et al.

OTHER PUBLICATIONS

Zhang et al. (Langmuir 2012, 28, 7055-7062 (2012).*
Fragoon et al. (Journal of Nanoscience and Nanotechnology vol. 12, 2337-2345 (2012)).*
English translation of CN103361044 (2013).*

* cited by examiner

*Primary Examiner* — David J Blanchard
*Assistant Examiner* — Garen Gotfredson
(74) *Attorney, Agent, or Firm* — Richard C. Litman

(57) ABSTRACT

The green synthesis of a reduced graphene oxide (rGO) silica ($SiO_2$) nanocomposite using *Nigella sativa* seed extract includes mixing a quantity of carbon source in an acid solution while stirring to obtain a solution; adding a first oxidant gradually into the solution to oxidize the soot and obtain a first suspension; stirring the first suspension while maintaining a temperature of the suspension to about 35° C.; adding plant seeds extract to the first suspension while raising the temperature of the suspension to about 60° C.; adding a second oxidant to the suspension to form the reduced graphene oxide nanoparticles; isolating the reduced graphene oxide nanoparticles by centrifugation; suspending the reduced graphene oxide nanoparticles in water; adding a solution comprising tetraethyl orthosilicate (TEOS), concentrated aqueous ammonia solution and a plant seeds extract under ultrasonication; and increasing the temperature to about 90° C. to form reduced graphene oxide-silicon dioxide nanocomposite suspension.

5 Claims, 6 Drawing Sheets

GREEN SYNTHESIS OF REDUCED GRAPHENE OXIDE SILICA NANOCOMPOSITE USING *NIGELLA SATIVA* SEEDS EXTRACT

BACKGROUND OF THE INVENTION

1. Field of the Invention

The present invention relates to graphene oxide nanocomposites, and particularly to green synthesis of a reduced graphene oxide (rGO) silica ($SiO_2$) nanocomposite using *Nigella sativa* seed extract.

2. Description of the Related Art

One of the recent advances in pharmacological research has been the usage of novel drug delivery systems and also the increasing application of monoclonal antibodies and oligonucleotides for therapeutic purpose. The functionalized nano-sized graphene has been used as a drug carrier for in vitro intracellular delivery of anticancer chemotherapy drugs. It has been found that nano-graphene with a biocompatible polyethylene glycol (PEG) coating displays high passive in vivo tumor uptake and could be used for effective photo-thermal ablation of tumors in a mouse model. On the other hand, many groups have developed graphene-based biosensors to detect various biomolecules via different mechanisms. Graphene-based nanomedicine, although still in its infancy, appears to be encouraging and may bring novel opportunities for future disease diagnosis and treatment.

Graphene is an atom thick monolayer of carbon atoms arranged in a two dimensional honeycomb structure and it is a basic building block for other graphitic materials such as graphite and carbon nanotubes. Because of their unique and desirable electrical, optical, mechanical and chemical characteristics, graphene, graphene oxide (GO), and reduced graphene oxide (rGO) have been extensively studied for a variety of applications such as nanoelectronics, sensors, energy storage, nanocomposites, etc. including biomedicine. The potential of graphene as nanocarriers for drug delivery, gene delivery and nanomedicine have been demonstrated for possible cancer therapies. In addition, the improved synthesis and versatile surface modification of graphene has opened up new avenues for research on the nanoscale. In this regard, using "green" methods in the synthesis of nanoparticles and nanocomposites has received attention as conventional chemical methods are expensive and require the use of hazardous chemical and organic solvents.

Thus, green synthesis of a reduced graphene oxide (rGO) silica ($SiO_2$) nanocomposite using *Nigella sativa* seed extract solving the aforementioned problems is desired.

SUMMARY OF THE INVENTION

The green synthesis of a reduced graphene oxide (rGO) silica ($SiO_2$) nanocomposite using *Nigella sativa* seed extract comprises the steps of mixing a quantity of carbon source in an acid solution while stirring to obtain a solution; adding a first oxidant gradually into said solution to oxidize the soot and obtain a first suspension; stirring the first suspension while maintaining a temperature of said suspension to about 35° C.; adding *Nigella sativa* seed to the first suspension while raising the temperature of the suspension to about 60° C.; adding a second oxidant to said suspension to form the reduced graphene oxide nanoparticles; isolating the reduced graphene oxide nanoparticles by centrifugation; suspending the reduced graphene oxide nanoparticles in water to form a second suspension; ultrasonicating the second suspension for about 60 minutes; centrifuging the second suspension at about 3000 rpm to remove any aggregates; adding a solution comprising tetraethyl orthosilicate (TEOS), concentrated aqueous ammonia solution, and *Nigella sativa* seed extract under ultrasonication conditions to obtain a third suspension; increasing the temperature of the third suspension to about 90° C. while stirring gradually for about 3 hours to form reduced graphene oxide-silicon dioxide nanocomposite suspension; and isolating the graphene oxide-silicon dioxide nanocomposite by filtration.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
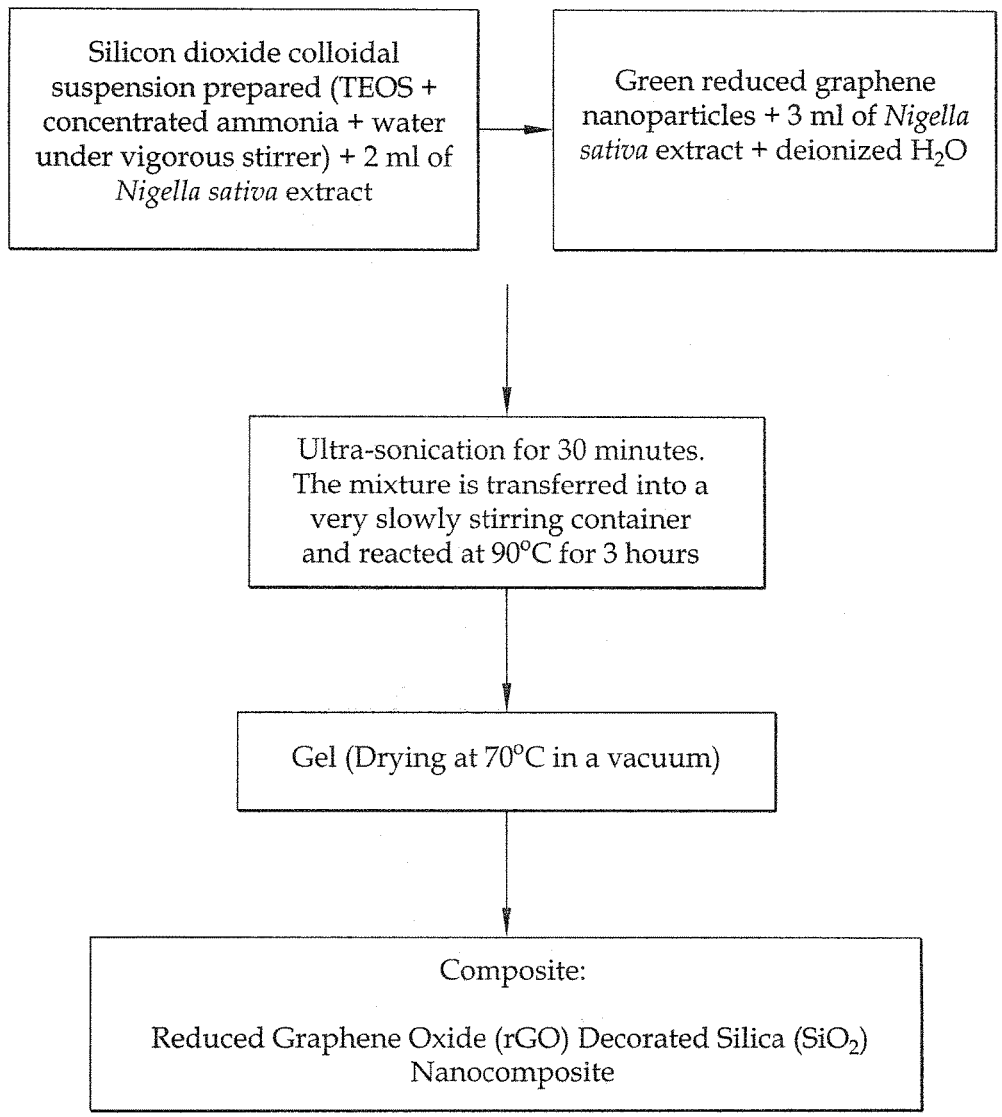
FIG. 1 shows the schematic for preparing green reduced graphene oxide/$SiO_2$ nanocomposite using *Nigella sativa* seed extract by a sol-gel method.

The green synthesis of a reduced graphene oxide (rGO) silica ($SiO_2$) nanocomposite using *Nigella sativa* seed extract comprises the steps of mixing a quantity of carbon source in an acid solution while stirring to obtain a solution; adding a first oxidant gradually into said solution to oxidize the soot and obtain a first suspension; stirring the first suspension while maintaining a temperature of said suspension to about 35° C.; adding *Nigella sativa* seed to the first suspension while raising the temperature of the suspension to about 60° C.; adding a second oxidant to said suspension to form the reduced graphene oxide nanoparticles; isolating the reduced graphene oxide nanoparticles by centrifugation; suspending the reduced graphene oxide nanoparticles in water to form a second suspension; ultrasonicating the second suspension for about 60 minutes; centrifuging the second suspension at about 3000 rpm to remove any aggregates; adding a solution comprising tetraethyl orthosilicate (TEOS), concentrated aqueous ammonia solution, and *Nigella sativa* seed extract under ultrasonication conditions to obtain a third suspension; increasing the temperature of the third suspension to about 90° C. while stirring gradually for about 3 hours to form reduced graphene oxide-silicon dioxide nanocomposite suspension; and isolating the graphene oxide-silicon dioxide nanocomposite by filtration.

The method of synthesizing reduced graphene oxide silica nanocomposite using a plant seed extract can further comprise washing the graphene oxide-silicon dioxide nanosuspension with water and drying the suspension at about 70° C. in an oven. The carbon source for producing the reduced graphene oxide can be soot collected from girdle which is formed during bakery. The plant seed extract used in the synthesis of reduced graphene oxide nanoparticles are obtained from the plant *Nigella sativa*. The step of adding the *Nigella sativa* seed extract can be performed at a temperature of the suspension of about 60° C. for about 15 minutes. The acid solution can be sulfuric acid. Generally, the first oxidant can be potassium permanganate and the second oxidant can be hydrogen peroxide.

The reduced graphene oxide nanoparticles, which are produced from the synthesis method, can have a mean diameter in the range of from about 5 nm to about 100 nm across the largest dimension. Typically, the graphene oxide nanoparticles can have one or more shapes selected from the group consisting of spherical-shaped, spheroidal-shaped, elongated/spherical shaped, rod-shaped and/or faceted shaped.

The reduced graphene oxide nanoparticles can be used in inhibiting cancer cell proliferation. For example a method of inhibiting the growth or proliferation of a cancer cell comprises the step of contacting the cancer cell with an effective amount of the reduced graphene oxide/silica nanoparticles synthesized according to the method described herein. The cancer cell can include a breast carcinoma cell or a colon carcinoma cell.

As used herein the term "nanoparticle" refers to a particle having at least one dimension sized between 1 and 100 nanometers. By the term "effective amount", it is understood that, with respect to, for example, pharmaceuticals, a pharmaceutically effective amount is contemplated. A pharmaceutically effective amount is the amount or quantity of active ingredient which is enough for the required or desired therapeutic response, or in other words, the amount, which is sufficient to elicit an appreciable biological response when administered to a patient.

As used herein, the term "seed extract" encompasses, for example, any chemical or combination of chemicals found in the seeds of the plant, including the derivatives of the compounds found in the seeds via chemical reaction. The "seed extract" can be obtained from the plant by any process, for example, cold water extraction, hot water extraction, extraction with an organic solvent, and/or extraction with a supercritical solvent. The preferred method of extraction of *Nigella sativa* seed extract is using boiling water as described below.

*Nigella sativa*, often called black cumin, is an annual flowering plant in the family Ranunculaceae, native to south and southwest Asia. *Nigella sativa* grows to 20-30 cm tall, with finely divided, linear leaves.

The following examples will further illustrate the green synthesis of a reduced graphene oxide (rGO) silica ($SiO_2$) nanocomposite using *Nigella sativa* seed extract.

Example 1

Preparation of Extract from *Nigella Sativa* Seeds

*Nigella sativa* seeds were washed several times with distilled water. Then about 30 grams of coarsely ground *Nigella sativa* seeds were taken and boiled in 150 mL of double distilled water for about 5 min. The extract was centrifuged and then filtered. The filtrate was collected and stored at 4° C. until further use.

Example 2

Green Synthesis of Reduced Graphene Oxide (rGO) Nanoparticles Decorated with Silica ($SiO_2$) Nanocomposite Using *Nigella sativa* Seed Extract Soot was collected from girdle which formed during bakery of Abray, a local and traditional paste used as drinker in Ramadan month in Sudan. Graphene oxide (GO) was prepared according to the modified Hummer's method. In detail, 1 g of soot was mixed with 50 mL $H_2SO_4$ and stirred for 5 min. Next, 5 g of potassium permanganate, ($KMnO_4$), was very slowly added in an ice bath. The suspension was again stirred at 35° C. for 10 min. The temperature of the mixture was adjusted to a constant 60° C. for 15 min while the *Nigella sativa* seed extract was added continuously so that the volume of the suspension was 150 mL Then 5 mL of $H_2O_2$ was added after 5 min. The reaction product was centrifuged and washed with deionized water and 5% HCl solution repeatedly. Finally, the product was dried at 80° C.

The graphite oxide was then exfoliated by ultra-sonication. For this purpose, GO powder dispersed in a known volume of water was subjected to ultra-sonication for 60 min to give a stable suspension of GO and then centrifuged at 3000 rpm for 30 min to remove any aggregates remained in the transparent exfoliated GO suspension. Secondly, 12.68 mL of tetraethyl orthosilicate (TEOS) was hydrolyzed with 2.82 mL concentrated ammonia, 84.5 mL water and 2 ml of *Nigella sativa* seed extract were added into 10 mL above solution and the solution was mixed by ultra-sonication for 30 min. The mixture was transferred into a very slowly stirrer and reacted at 90° C. for 3 h. The resulting rGO-$SiO_2$ nano suspension was filtered and washed with plenty of water and dried at 70° C. FIG. 1 illustrates schematically the preparation of green reduced graphene Oxide/$SiO_2$ nanocomposite using *Nigella sativa* seeds extract by sol gel method.

The produced nanocomposite was characterized by Transmission electron microscopy (TEM) (JEM-1011, JEOL, Japan) also Scanning Electron Microscopy (SEM) (JEOL-FE SEM) was used to characterize the shape and morphologies of formed biogenic synthesized silver nanoparticles using JEOL-FE SEM; in addition to X-ray diffractometer (XRD), Bruker D8 ADVANCE, while the size of synthesized nanoparticles was analyzed through Zetasizer, Nano series, HT Laser, ZEN3600 (Molvern Instrument, UK). JEOL-FE SEM and Energy Dispersive Spectrometer (EDS) analysis was performed for the confirmation of elemental silicon, oxygen and carbon.

Figure 2:
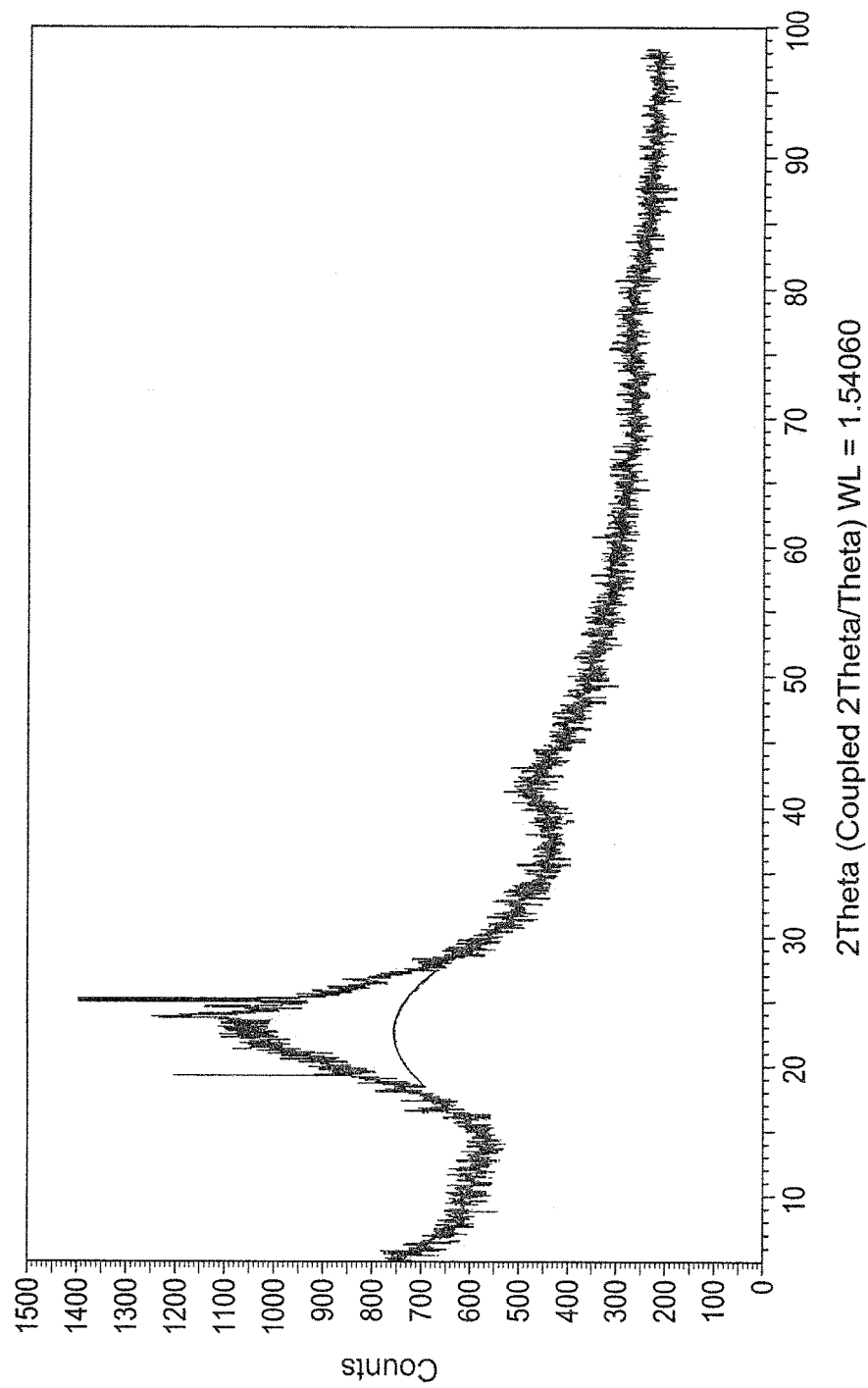
FIG. 2 shows the X-ray diffraction pattern of green synthesized reduced graphene oxide/$SiO_2$ nanocomposite nanoparticles using *Nigella sativa* seed extract.
Figure 3:
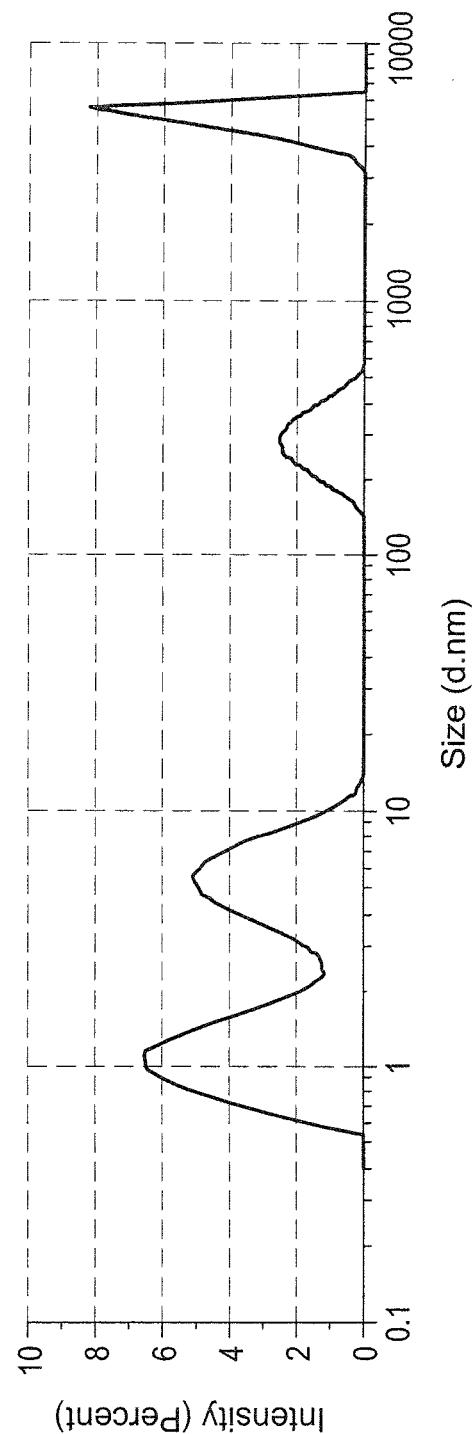
FIG. 3 shows a particle size distribution green synthesized reduced graphene oxide/$SiO_2$ nanocomposite using *Nigella sativa* seed extract.
Figure 4B:
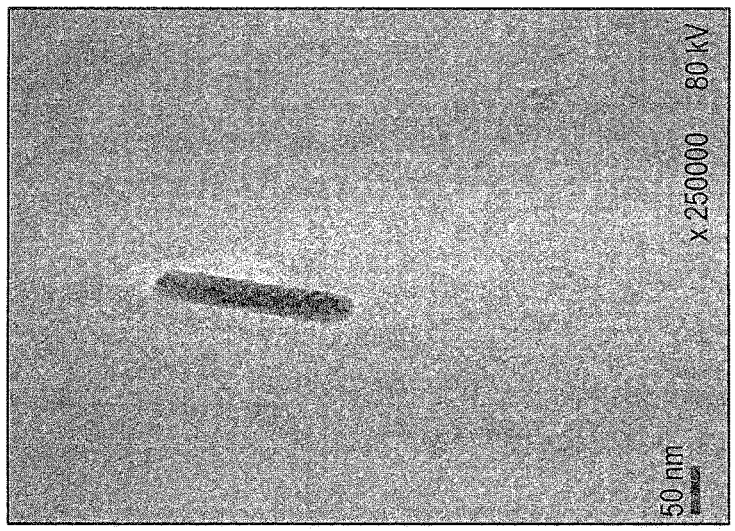
FIGS. 4A and 4B show transmission electron micrographs (TEM) of the reduced graphene oxide decorated with $SiO_2$ nanocomposite using *Nigella sativa* seed extract.
Figure 4A:
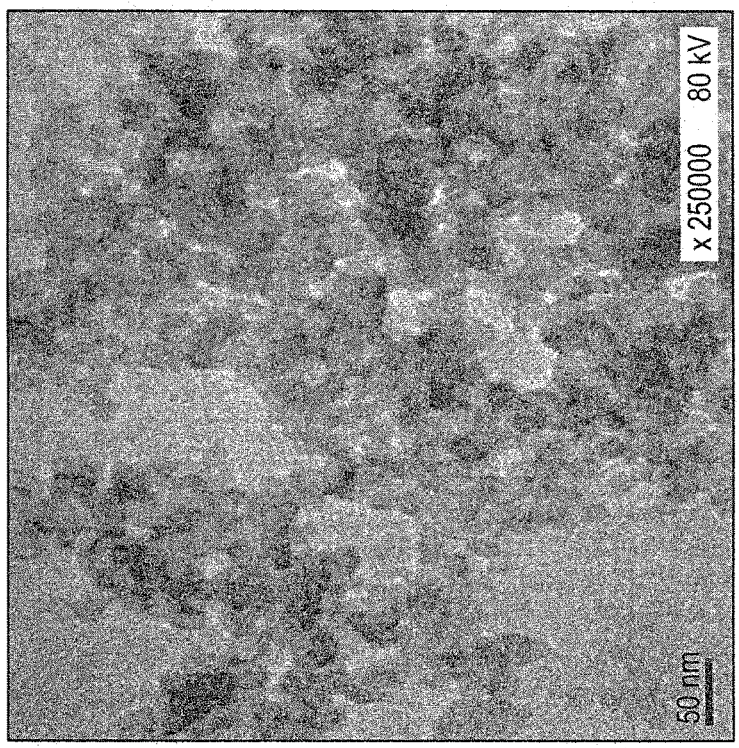
Figure 5:
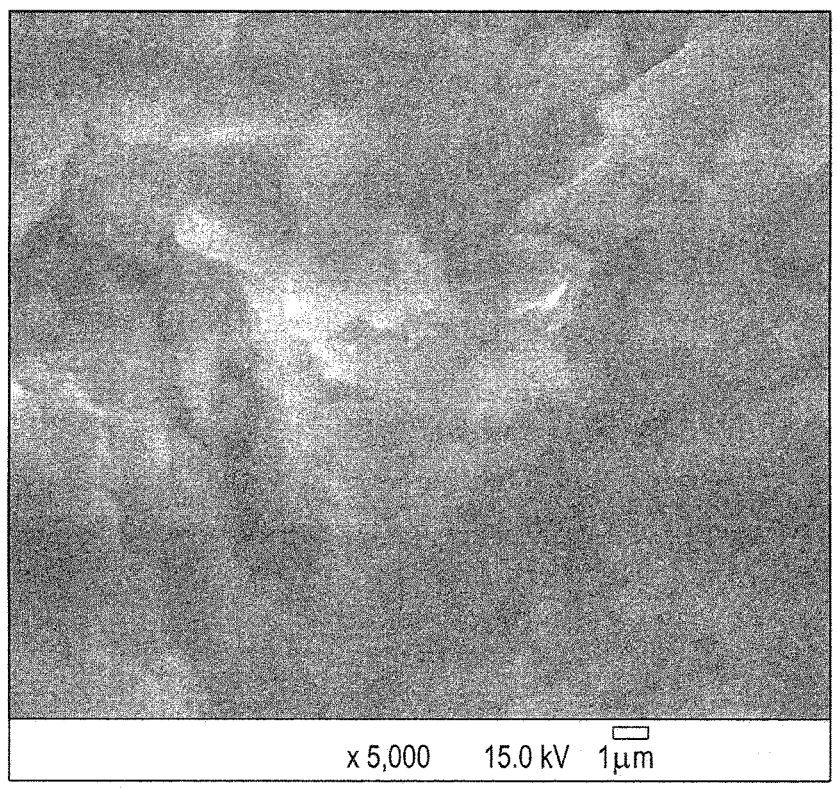
FIG. 5 shows a scanning electron micrograph (SEM) of green synthesized reduced graphene oxide decorated with $SiO_2$ nanocomposite using *Nigella sativa* seed extract.
Figure 6:
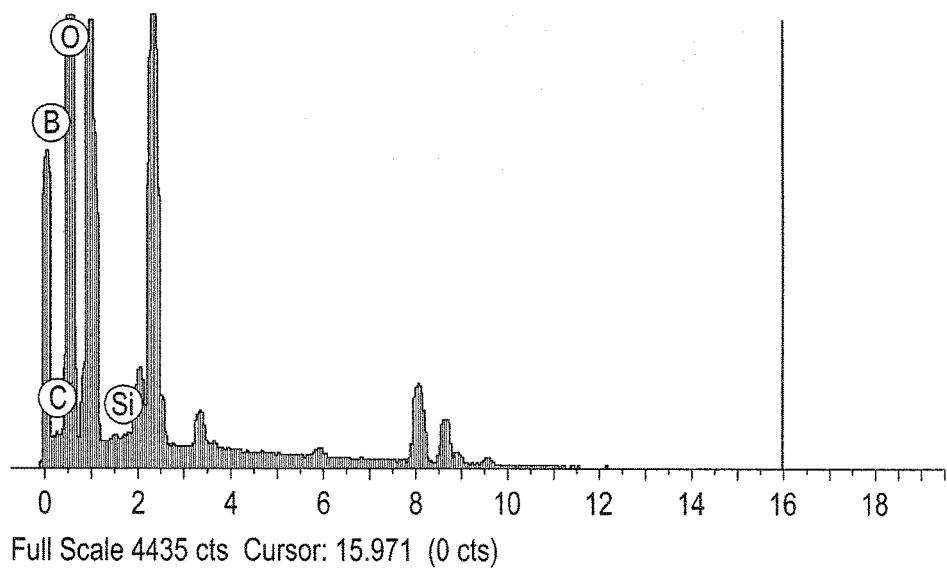
FIG. 6 shows the EDS pattern of green synthesized reduced graphene oxide nanoparticles using *Nigella sativa* seed extract with four dominant peaks for boron, carbon, oxygen and silicon atoms, respectively.

FIG. 2 shows the XRD pattern of green synthesized reduced graphene oxide/$SiO_2$ nanocomposite using *Nigella sativa* seeds extract. FIG. 3 shows the particle size distribution of green synthesized reduced graphene oxide/$SiO_2$ nanocomposite using *Nigella sativa* seeds extract. Three peaks having Z-average sizes of 1.176 nm (peak 1), 5.488 nm (peak 2) and 5086 nm (peak 3) having intensities of 39.8%, 32.7% and 15.4% respectively were found. The Energy Dispersive Spectrometer (EDS) analysis was performed for the confirmation of elemental silicon, oxygen and carbon. The transmission electron micrograph (TEM) images of green synthesized reduced graphene oxide decorated with $SiO_2$ nanocomposite using *Nigella sativa* are shown in FIG. 4. The shapes can be spherical, spheroidal, rod-like etc. having a dimension of at least 5 nm to 100 nm. FIG. 5 shows the scanning electron microscopy (SEM) images of green synthesized reduced graphene oxide decorated with $SiO_2$ nanocomposite using *Nigella sativa*. FIG. 6 shows the energy dispersive spectroscopy (EDS) pattern of green synthesized reduced graphene oxide decorated with $SiO_2$ nanocomposite using *Nigella sativa* with four dominant peaks for Boron, carbon, oxygen and silicon atoms, respectively. Table 1 provides the EDS results showing the percentage of elements present in reduced graphene oxide nanoparticles suspension.

TABLE 1

| Element | Weight % | Atomic % |
|---|---|---|
| B | 3.81 | 5.39 |
| C | 8.45 | 10.77 |
| O | 87.42 | 83.66 |
| Si | 0.32 | 0.17 |
| TOTALS | 100.00 | |

Example 3

Antitumor Activity Assay

The tested human carcinoma cell lines were obtained from the American Type Culture Collection (ATCC, Rockville, Md.). The cells were grown on RPMI-1640 medium supplemented with 10% inactivated fetal calf serum and 50 µg/ml gentamycin. The cells were maintained at 37° C. in a humidified atmosphere with 5% $CO_2$ and were subcultured two to three times a week.

For antitumor assays, the tumor cell lines were suspended in medium at concentration $5 \times 10^4$ cell/well in Corning® 96-well tissue culture plates, then incubated for 24 h. The tested compounds were then added into 96-well plates (six replicates) to achieve eight concentrations for each compound. Six vehicle controls with media or 0.5% DMSO were run for each 96 well plate as a control. After incubating for 24 h, the numbers of viable cells were determined by the MTT test. Briefly, the media was removed from the 96 well plates and replaced with 100 µl of fresh culture RPMI 1640 medium without phenol red then 10 µl of the 12 mM MTT stock solution (5 mg of MTT in 1 mL of PBS) to each well including the untreated controls. The 96 well plates were then incubated at 37° C. and 5% $CO_2$ for 4 h. An 85 µl aliquot of the media was removed from the wells, and 50 µl of DMSO was added to each well and mixed thoroughly with the pipette and incubated at 37° C. for 10 min. Then, the optical density was measured at 590 nm with the microplate reader (Sun Rise, TECAN, Inc., USA) to determine the number of viable cells and the percentage of viability was calculated using the following equation (1):

$$\text{Percentage of Viability} = \left[1 - \frac{ODt}{ODc}\right] \times 100 \quad (1)$$

Figure 7:
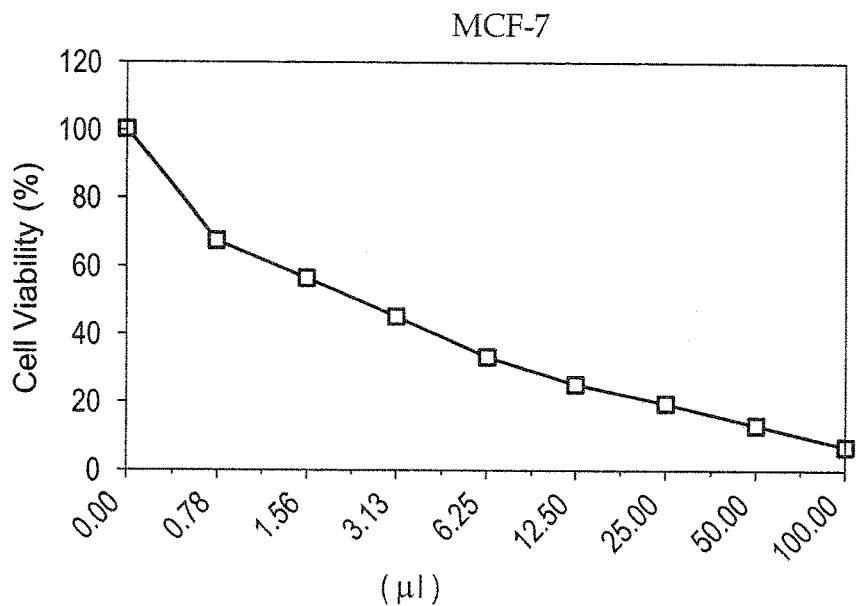
FIG. 7 is a plot of the cytotoxic activity of reduced graphene graphene oxide/$SiO_2$ nanocomposite synthesized from *Nigella sativa* seed extract suspension against breast carcinoma cells (MCF-7 cell line).

In equation 1, ODt is the mean optical density of wells treated with the tested sample and ODc is the mean optical density of untreated cells. The relation between surviving cells and drug concentration is plotted to get the survival curve of each tumor cell line after treatment with the specified compound. FIG. 7 shows the cytotoxic activity of reduced graphene oxide/$SiO_2$ nanocomposite synthesized from *Nigella sativa* seeds extract suspension against breast carcinoma cells (MCF-7) cell line. Table 2 shows the inhibitory activity of reduced graphene oxide synthesized from *Nigella sativa* extract against Breast carcinoma cells was detected under these experimental conditions with $IC_{50}$-2.67 µl. The 50% inhibitory concentration ($IC_{50}$), the concentration required to cause toxic effects in 50% of intact cells, was estimated from graphic plots of the dose response curve for each conc. using Graphpad Prism software (San Diego, Calif. USA) (Mosmann, 1983; Elaasser et al., 2011).

TABLE 2

| Sample conc. (µl) | Viability % (3 Replicates) | | | | Inhibition % | Standard Deviation (±) |
|---|---|---|---|---|---|---|
| | 1st | 2nd | 3rd | Mean | | |
| 100 | 7.34 | 6.89 | 6.38 | 6.87 | 93.13 | 0.48 |
| 50 | 11.67 | 12.36 | 14.25 | 12.76 | 87.24 | 1.34 |
| 25 | 18.42 | 19.82 | 19.73 | 19.32 | 80.68 | 0.78 |
| 12.5 | 24.83 | 26.78 | 22.97 | 24.86 | 75.14 | 1.91 |
| 6.25 | 32.71 | 30.95 | 35.59 | 33.08 | 66.92 | 2.34 |
| 3.125 | 44.92 | 41.87 | 48.19 | 44.99 | 55.01 | 3.16 |
| 1.56 | 53.21 | 58.42 | 56.78 | 56.14 | 43.86 | 2.66 |
| 0.78 | 69.45 | 68.29 | 64.32 | 67.35 | 32.65 | 2.69 |
| 0 | 100 | 100 | 100 | 100 | 0.00 | |

Figure 8:
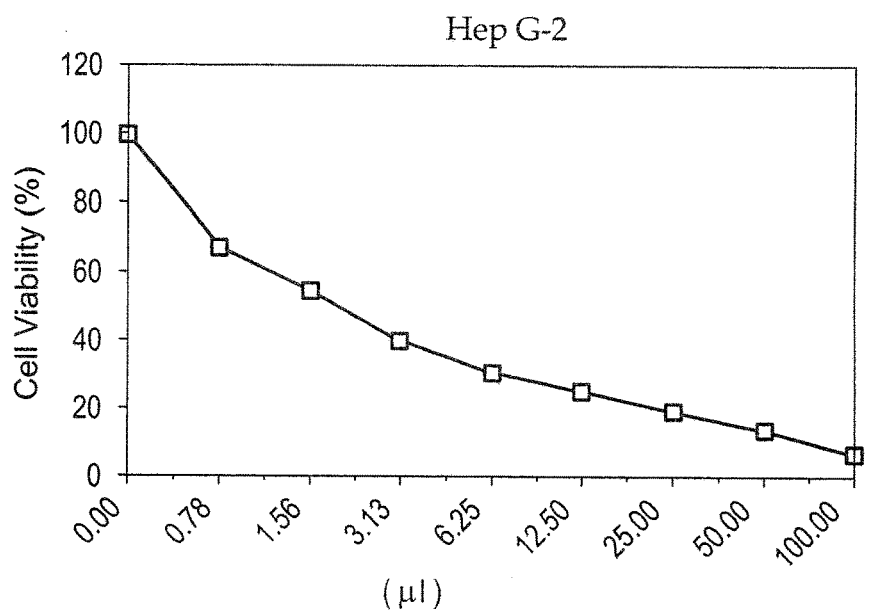
FIG. 8 is a plot of the cytotoxic activity of reduced graphene oxide $SiO_2$ nanocomposite synthesized from *Nigella sativa* seed extract suspension against Hepatocellular carcinoma cells (HepG-2 cell line).

FIG. 8 shows the cytotoxic activity of reduced graphene oxide/$SiO_2$ nanocomposite synthesized from *Nigella sativa* seeds extract suspension against Hepatocellular carcinoma cells (HepG-2 cell line). Table 3 shows the inhibitory activity of reduced graphene oxide/$SiO_2$ nanocomposite synthesized from *Nigella sativa* extract against Hepatocellular carcinoma cells was detected under these experimental conditions with $IC_{50}$=2.1 µl. The 50% inhibitory concentration ($IC_{50}$), the concentration required to cause toxic effects in 50% of intact cells, was estimated from graphic plots of the dose response curve for each conc. using Graphpad Prism software (San Diego, Calif. USA) (Mosmann, 1983; Elaasser et al., 2011).

| Sample conc. (µl) | Viability % (3 Replicates) | | | | Inhibition % | Standard Deviation (±) |
|---|---|---|---|---|---|---|
| | 1st | 2nd | 3rd | Mean | | |
| 100 | 7.24 | 6.13 | 6.94 | 6.77 | 93.23 | 0.57 |
| 50 | 13.65 | 14.91 | 12.86 | 13.81 | 86.19 | 1.03 |
| 25 | 19.82 | 17.56 | 20.74 | 19.37 | 80.63 | 1.64 |
| 12.5 | 26.43 | 23.84 | 25.19 | 25.15 | 74.85 | 1.30 |
| 6.25 | 30.75 | 28.92 | 32.71 | 30.79 | 69.21 | 1.90 |
| 3.125 | 39.46 | 37.61 | 42.87 | 39.98 | 60.02 | 2.67 |
| 1.56 | 51.43 | 54.12 | 58.93 | 54.83 | 45.17 | 3.80 |
| 0.78 | 69.27 | 68.48 | 64.22 | 67.32 | 32.68 | 2.72 |
| 0 | 100 | 100 | 100 | 100 | 0.00 | |

Thus the above examples illustrate a simple, non-toxic, cost-effective, quick, and environmentally friendly synthesis approach for the reduced graphene oxide-silicon dioxide (rGO-$SiO_2$) nanocomposites using *Nigella sativa*. It is believed that the (rGO-$SiO_2$) nanocomposites could be promising in the fields of drug delivery, parasitology, tissue engineering (TE), antibacterial agents, cancer therapy, sensors imaging including diagnostics.

It is to be understood that the present invention is not limited to the embodiments described above, but encompasses any and all embodiments within the scope of the following claims.

We claim:

1. A method of green synthesis of a reduced graphene oxide (rGO) silica ($SiO_2$) nanocomposite, comprising the sequential steps of:
   mixing a quantity of soot in an acid while stirring to obtain a solution;
   adding a first oxidant gradually into the solution to oxidize the soot and obtain a first suspension;
   stirring the first suspension while maintaining a temperature of the suspension at about 35° C.;
   adding *Nigella sativa* seed extract to the first suspension while raising the temperature of the suspension to about 60° C.;
   adding a second oxidant to the suspension to form reduced graphene oxide nanoparticles;
   isolating the formed reduced graphene oxide nanoparticles by centrifugation;
   suspending the reduced graphene oxide nanoparticles in water to form a second suspension;
   ultrasonicating the second suspension for about 60 minutes;
   centrifuging the second suspension at about 3000 rpm to remove any aggregates;
   adding a solution comprising tetraethyl orthosilicate (TEOS), concentrated aqueous ammonia solution and *Nigella sativa* seed extract under ultrasonication conditions to the second suspension to obtain a third suspension;
   increasing the temperature of the third suspension to about 90° C. while stirring gradually for about 3 hours to form reduced graphene oxide-silicon dioxide nanocomposite suspension; and
   isolating the reduced graphene oxide-silicon dioxide nanocomposite by filtration.

2. The method of green synthesis of a reduced graphene oxide (rGO) silica (SiO2) nanocomposite according to claim 1, further comprising the steps of washing the graphene oxide-silicon dioxide nanocomposite suspension with water and drying the suspension at about 70° C.

3. The method of green synthesis of a reduced graphene oxide (rGO) silica ($SiO_2$) nanocomposite according to claim 1, wherein the acid is sulfuric acid.

4. The method of green synthesis of a reduced graphene oxide (rGO) silica ($SiO_2$) nanocomposite according to claim 1, wherein the first oxidant is potassium permanganate.

5. The method of green synthesis of a reduced graphene oxide (rGO) silica ($SiO_2$) nanocomposite according to claim 1, wherein the second oxidant is hydrogen peroxide.

* * * * *